United States Patent
Shirao et al.

(10) Patent No.: US 9,241,884 B2
(45) Date of Patent: Jan. 26, 2016

(54) REDISPERSIBLE POWDER-DISPERSED COSMETIC

(71) Applicant: SHISEIDO COMPANY, LTD., Tokyo (JP)

(72) Inventors: Masayuki Shirao, Yokohama (JP); Shigeru Mugikura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 6 days.

(21) Appl. No.: 14/372,896

(22) PCT Filed: Dec. 25, 2012

(86) PCT No.: PCT/JP2012/083393
§ 371 (c)(1),
(2) Date: Jul. 17, 2014

(87) PCT Pub. No.: WO2013/114766
PCT Pub. Date: Aug. 8, 2013

(65) Prior Publication Data
US 2014/0357721 A1 Dec. 4, 2014

(30) Foreign Application Priority Data

Feb. 2, 2012 (JP) ................................. 2012-020547
Dec. 18, 2012 (JP) ................................. 2012-275277

(51) Int. Cl.

| | | |
|---|---|---|
| A61K 8/362 | (2006.01) | |
| A61K 8/368 | (2006.01) | |
| A61K 8/73 | (2006.01) | |
| A61K 8/25 | (2006.01) | |
| A61K 8/26 | (2006.01) | |
| A61K 8/60 | (2006.01) | |
| A61K 8/86 | (2006.01) | |
| A61K 8/92 | (2006.01) | |
| A61K 8/02 | (2006.01) | |
| A61Q 19/00 | (2006.01) | |

(52) U.S. Cl.
CPC ................. *A61K 8/25* (2013.01); *A61K 8/0241* (2013.01); *A61K 8/26* (2013.01); *A61K 8/362* (2013.01); *A61K 8/368* (2013.01); *A61K 8/60* (2013.01); *A61K 8/731* (2013.01); *A61K 8/86* (2013.01); *A61K 8/922* (2013.01); *A61Q 19/00* (2013.01); *A61Q 19/008* (2013.01)

(58) Field of Classification Search
CPC ......... A61K 8/362; A61K 8/368; A61K 8/25; A61K 8/26; A61Q 19/00; A61Q 19/008
See application file for complete search history.

(56) References Cited

FOREIGN PATENT DOCUMENTS

| | | |
|---|---|---|
| JP | 4-360830 | 12/1992 |
| JP | H11116427 | 4/1999 |
| JP | 2001-340748 | 12/2001 |
| JP | 2004-244402 | 9/2004 |
| JP | 2013-177366 | 9/2013 |
| JP | 5373177 | 9/2013 |

OTHER PUBLICATIONS

PCT/JP2012/083393 International Search Report mailed Apr. 9, 2013, 1 page—English, 2 pages—Japanese.
Notice of Reasons for Rejection dated Apr. 5, 2013. 2 pages—English; 2 pages—Japanese.
Written Argument dated May 9, 2013, 1 page—English; 7 pages—Japanese.
Written Amendment dated May 9, 2013, 1 page—English; 2 pages—Japanese.
JPO Decision to Grant dated Sep. 6, 2013, 3 pages—English; 3 pages—Japanese.
Granted Claims, 1 page—English; and certificate of translation. Jul. 24, 2014.

*Primary Examiner* — Bethany Barham
*Assistant Examiner* — Barbara Frazier
(74) *Attorney, Agent, or Firm* — Andrew F. Young, Esq.; Lackenbach Siegel, LLP

(57) ABSTRACT

Provided is a redispersible powder-dispersed cosmetic which has a clear supernatant when unused, can exhibit good powder redispersibility when shaken upon use, has a good sensation, e.g., smoothness and non-stickiness, upon application to the skin, and has an excellent effect of dissolving/removing keratotic plugs. The cosmetic is characterized by comprising (A) succinic acid and/or a salt thereof, (B) bentonite and (C) a hydrophilic surfactant. Particularly preferably, the cosmetic additionally comprises a cellulose powder. It is preferred that the component (A), i.e., succinic acid and/or the salt thereof, is contained in an amount of 0.01 to 10.0 mass % relative to the total amount of the cosmetic.

2 Claims, No Drawings

REDISPERSIBLE POWDER-DISPERSED COSMETIC

TECHNICAL FIELD

The present invention relates to a redispersible powder-dispersed cosmetic that is applied on the skin after shaking to disperse powder components, wherein the cosmetic has an effect on dissolving and removing keratotic plugs. Further specifically, the present invention relates to a redispersible powder-dispersed cosmetic may provide a good powder redispersibility when shaken for use while being to give a clear supernatant when not-in-use, a good feeling-in-use such as smoothness and non-stickiness with dry-feeling when applied to the skin, and further an excellent effect on dissolving and removing keratotic plugs.

BACKGROUND ART

Keratotic plugs occur by accumulation and coagulation of sebum secreted from the sebaceous gland and old keratin in the surrounding area in the pores, which is responsible for acne and darkened pores. A primary treatment method to remove keratotic plugs so far includes a step of adhering a tape-agent on the skin or covering the pores with a pack-agent and then a step of absorbing the keratotic plugs thereto followed by a step of peeling the tape-agent or pack-agent off together every keratotic plugs. However, such method may cause pain when the tape-agent or the pack-agent is peeled off and may remove not only the keratotic plugs but also keratin from the healthy skin surface, which sometimes results in occurrence of skin problems. Thus, a method for effectively removing keratotic plugs from the pores has been suggested, wherein organic acids such as lactic acid and citric acid and/or salts thereof are used without resorting to such physical removing method (Patent Document 1.)

Meanwhile, cosmetics that contain powder components are shaken to redisperse the powder components upon use, i.e. redispersible powder-dispersed cosmetics, are known. As powder components, inorganic powders such as talc, titanium dioxide, and silicon dioxide, and/or organic powders such as nylon powder and polyethylene are used for the redispersible powder-dispersed cosmetics in order to suppress stickiness and impart smooth and greaseless feeling. However, when some of these powders are formulated in non-emulsified cosmetics such as skin lotions, the powders may rub against one another and as results cause stiffness, or powders may rub directly against the skin and as results harm the stratum corneum. Thus, use of spherical cellulose powder having relatively a low powder-hardness has been suggested (Patent Document 2.)

When an organic acid such as citric acid and/or a salt thereof is formulated in a redispersible powder-dispersed cosmetic containing powder components such as spherical cellulose powder in order to obtain a redispersible powder-dispersed cosmetic having an effect on dissolving and removing keratotic plugs, while keeping the advantage of an excellent feeling-in-use upon application on the skin, a sufficient feeling-in-use may not be achieved in spite of the presence of the powder components. Further, even if the cosmetic is shaken for use, powder components tend to remain at the bottom of the container, leading to unsatisfactory powder redispersion.

CITATION LIST

Patent Literature

Patent Literature 1: Japanese Patent Laid-Open No. H4-360830

Patent Literature 2: Japanese Patent Laid-Open No. H11-116427

SUMMARY OF INVENTION

Technical Problem

The present invention has been completed in consideration of the drawbacks of the prior arts, and one object of the present invention is to provide a redispersible powder-dispersed cosmetic having a good powder redispersibility when shaken for use while being to give a clear supernatant when not-in-use, a good feeling-in-use such as smoothness and non-stickiness with dry-feeling when applied to the skin, and further an excellent effect on dissolving and removing keratotic plugs.

Solution to Problem

After intensive studies, the present inventors have found that a cosmetic having an excellent feeling-in-use, an excellent powder redispersibility, and an excellent effect on dissolving and removing keratotic plugs can be obtained; when succinic acid and/or a salt thereof as an active for dissolving and removing keratotic plugs is used, and further a bentonite and a hydrophilic surfactant are formulated; and thereby completed the present invention.

Specifically, the present invention is summarized as follows.

(1) A redispersible powder-dispersed cosmetic comprising:

(A) succinic acid and/or a salt thereof, (B) a bentonite, and (C) a hydrophilic surfactant.

(2) A redispersible powder-dispersed cosmetic according to (1), further comprising cellulose powder.

(3) A redispersible powder-dispersed cosmetic according to (1) or (2), wherein (A) succinic acid and/or a salt thereof is formulated at 0.01 to 10.0% by mass of the total amount of the cosmetic.

Advantageous Effects of Invention

A redispersible powder-dispersed cosmetic in accordance with the present invention forms a clear supernatant when stored, exhibits good powder redispersibility when shaken for use, provides a good feeling-in-use such as smoothness and non-stickiness with dry-feeling when applied to the skin, and has an excellent effect on dissolving and removing keratotic plugs. The cosmetic thus can remove keratotic plugs without harming the skin, make pores inconspicuous, and further provide a comfortable feeling-in-use.

DESCRIPTION OF EXAMPLES

A redispersible powder-dispersed cosmetic of the present invention comprises (A) succinic acid and/or a salt thereof, (B) a bentonite, and (C) a hydrophilic surfactant. Hereinafter, the present invention will be described in detail.

<(A) Succinic Acid and/or a Salt Thereof>

Succinic acid used in the present invention is a known substance represented by the following formula:

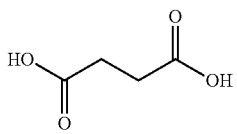

[Formula 1]

Further, a salt of succinic acid used in the present invention may include a salt such as a metal salt, including sodium, potassium, and calcium that are commonly used in the industries of food, quasi-pharmaceuticals, and cosmetics, but not limited to.

The formulation amount of (A) succinic acid and/or a salt thereof is from 0.01 to 10.0% by mass and preferably from 0.05 to 5.0% by mass of the total amount of the redispersible powder-dispersed cosmetic. As trends, if the formulation amount thereof is less than 0.01% by mass, an effect on dissolving and removing keratotic plugs shall be insufficient, and if the formulation amount thereof is more than 10.0% by mass, a feeling-in-use shall be damaged due to roughness caused by an insoluble material. In some cases, a small amount of succinic acid and/or citric is used as a pH adjuster or pH stabilizer (a buffer) with their salts. Also in the present invention, when a small amount (less than about 0.5% by mass) of succinic acid and a salt thereof) is formulated, it is believed that these act as a buffer as well as exerting the effect on dissolving and removing keratotic plugs. Meanwhile, as the effect on dissolving and removing keratotic plugs may increase or decrease depending on the formulation amount of succinic acid and/or a salt thereof, more (for example, 0.7% by mass or more) than an appropriate amount of succinic acid and/or a salt thereof as a buffer (about 0.5% by mass) can be formulated to achieve an enhanced effect on dissolving and removing keratotic plugs, not to mention, and also succinic acid and/or a salt thereof can be formulated alone <(B) Bentonite>

A bentonite used in the present invention is a known water-swellable clay mineral mainly containing montmorillonite. The formulation amount of (B) a bentonite is from 0.01 to 10.0% by mass and preferably from 0.05 to 1.0% by mass of the total amount of the redispersible powder-dispersed cosmetic. If the amount is less than 0.01% by mass, feeling-in-use may decrease in some cases and such amount may be insufficient to achieve excellent powder redispersibility. Further, if the amount is more than 10.0% by weight, the cosmetic tends to be cakey.

<(C) Hydrophilic Surfactant>

(C) A hydrophilic surfactant used in the present invention shall be a surfactant having an HLB of 7 or higher. Such (C) hydrophilic surfactants may include polyoxyethylene alkyl ethers, polyoxyethylene/polyoxypropylene alkyl ethers, sorbitan fatty acid esters, glycerin monoalkyl esters, polyethylene glycol alkyl esters, polyoxyethylene hydrogenated castor oil, polyoxyethylene castor oil, polyoxyethylene glycerin alkyl esters, polyoxyethylene alkyl ether alkyl esters, polyoxyethylene sorbitan alkyl esters, polyglycerin alkyl esters, polyoxyethylene alkyl ether phosphates, pyroglutamic acid esters, dimethicone copolyols, alkaloyl alkyl taurates, alkaloyl glutamates, alkaloyl lactates, fatty acid soap, alkyl trimethyl ammonium chlorides, 2-alkyl-N-carboxymethyl-N-hydroxyethyl imidazolinium betaines, polyoxyethylene alkyl ether sulfates, and alkyl amide amines.

(C) The hydrophilic surfactant can be formulated in an amount of 0.01 to 10.0% by mass and preferably from 0.05 to 1.0% by mass of the total amount of the redispersible powder-dispersed cosmetic. If the formulation amount thereof is less than 0.01% by mass, it is insufficient to achieve excellent powder redispersibility, and if the formulation amount thereof is more than 10.0% by weight, it may cause stickiness and the feeling-in-use may be damaged.

To the redispersible powder-dispersed cosmetic according to the present invention, various components such as powder components, solid oils and fats, moisturizing agents, thickeners, metal ion sequestering agents, pigments, pH adjuster, skin nutrients, vitamins, preservatives, anti-oxidizing agents, anti-oxidizing aids, and perfumes, generally formulated in the industrial fields of cosmetics and quasi-pharmaceuticals, may be appropriately formulated as needed as long as the effects of the present invention are not compromised.

<Powder Components>

Formulatable powder components other than (B) a bentonite are powders usually used in cosmetics, irrespective of the particle structure that is porous or non-porous and so forth. Such powder components may include organic powders such as nylon, polyacrylonitrile, polyester, polystyrene, polypropylene, polystyrene, polyurethane, cellulose, and silicone resins; and inorganic powders such as magnesium silicate, calcium silicate, titanium dioxide, and anhydrous silicic acid. Of these, cellulose powder is preferably formulated and such cellulose powder consisting cellulose or cellulose esters can be employed. The powder component is preferably spherical and preferably has an average particle size thereof is 3 to 50 μm and a maximum particle size thereof is 100 μm or smaller, from the view of material handling during production, feeling-in-use, and powder redispersibility.

The powder components are formulated in an amount of from 0.01 to 10.0% by mass and preferably from 0.05 to 1.0% by mass of the total amount of the redispersible powder-dispersed cosmetic. If the formulation amount is less than 0.01% by mass, it shall be insufficient to achieve an excellent feeling-in-use, and if the formulation amount is more than 10.0% by mass, the cosmetic shall provide no enhancement for feeling-in-use and tends to be rather cakey.

The redispersible powder-dispersed cosmetic according to the present invention can be produced in accordance with a conventional method. The redispersible powder-dispersed cosmetic according to the present invention is a cosmetic, in which the powder usually precipitates, that should be shaken for use to redisperse the powder, and that can be a product such as a skin lotion, a beauty liquid, an essence, an aqueous foundation, and a shaving lotion.

EXAMPLES

Hereinbelow, the present invention is described in further details referring to Examples, but the present invention is not intended to be limited by these Examples. The formulation amount is expressed in % by mass, unless otherwise indicated. Prior to describing Examples, the evaluation method used in the present invention will be described.

(1) Smoothness

Five female panelists evaluated each sample applied on the cheeks as to smoothness. The effect is scored based on the following criteria.

A: Four to five panelists respond that the cosmetic is smooth.
B: Two to three panelists respond that the cosmetic is smooth.
C: One or none panelist responds that the cosmetic is smooth.

(2) Non-Stickiness with Dry-Feeling

Five female panelists evaluated each sample applied on the cheeks as to non-stickiness with dry-feeling. The effect is scored based on the following criteria.

A: Four to five panelists respond that the cosmetic has non-stickiness with dry-feeling.
B: Two to three panelists respond that the cosmetic has non-stickiness with dry-feeling.
C: One or none panelist responds that the cosmetic has non-stickiness with dry-feeling.

(3) White Turbidity of Supernatant

The test sample was shaken 120 times per minute with a stroke of 120 mm for 5 minutes in an incubator. Then, the sample was centrifuged using a centrifuge at 3000 rpm for five minutes. The white turbidity of the supernatant was visually evaluated based on the following criteria.
A: No white turbidity of the supernatant is observed.
B: Slightly white turbidity of the supernatant is observed.
C: White turbidity of the supernatant is obvious.

(4) Bottom Caking State

The test sample was centrifuged using a centrifuge at 3000 rpm for five minutes, and then it was shaken 10 times under the condition of 120 mm per stroke and 120 shakes per minute in an incubator. Caking state at the bottom of the container was evaluated based on the following criteria.

A: No powder is left at the bottom after shaking.
B: Powder remains more or less at the bottom after shaking.
C: Powder remains at the bottom after shaking.

(5) Effect of Dissolving and Removing Keratotic Plugs

Five female panelists applied the test sample on the cheeks twice a day for one month and evaluated dissolution and removal of keratotic plugs. The effect is scored based on the following criteria.
A: Four to five panelists respond that the cosmetic has an effect on dissolving and removing keratotic plugs.
B: Two to three panelists respond that the cosmetic has an effect on dissolving and removing keratotic plugs.
C: One or less panelist responds that the cosmetic has an effect on dissolving and removing keratotic plugs.

Redispersible powder-dispersed cosmetics (test samples) according to the formulations shown in Tables 1 and 2 below were prepared and each characteristic was evaluated based on the evaluation method described above. The combined results are shown in Tables 1 and 2.

TABLE 1

|  | Example 1 | Example 2 | Example 3 | Example 4 | Example 5 |
|---|---|---|---|---|---|
| Ion exchange water | Balance | Balance | Balance | Balance | Balance |
| Ethanol | 15 | 15 | 15 | 15 | 15 |
| Glycerin | 5 | 5 | 5 | 5 | 5 |
| 1,3-butylene glycol | 3 | 3 | 3 | 3 | 3 |
| PPG-13 decyltetradeceth-24 (HLB = 10) | 0.1 | — | — | — | — |
| Polyoxyethylene hydrogenated castor oil ((PEG = 60) (HLB = 14) *1 | — | 0.1 | — | — | — |
| Polyoxybutylene (15) polyoxyethylene (44) dimethyl dimer diol ether (HLB = 16) | — | — | 0.1 | — | — |
| polyoxyethylene (50) polyoxypropylene (40) block copolymer dimethyl ether (HLB = 17) | — | — | — | 0.1 | — |
| Polyglyceryl myristate (HLB = 15.7) | — | — | — | — | 0.1 |
| Bentonite*2 | 0.2 | 0.2 | 0.2 | 0.2 | 0.2 |
| Aluminum magnesium silicate*3 | — | — | — | — | — |
| Cellulose powder*4 | 1 | 1 | 1 | 1 | 1 |
| Talc | — | — | — | — | — |
| Sodium chloride | 0.2 | 0.2 | 0.2 | 0.2 | 0.2 |
| Phenoxyethanol | 0.3 | 0.3 | 0.3 | 0.3 | 0.3 |
| Succinic acid | 0.35 | 0.35 | 0.35 | 0.35 | 0.35 |
| Sodium succinate | 0.15 | 0.15 | 0.15 | 0.15 | 0.15 |
| Citric acid | — | — | — | — | — |
| Sodium citrate | — | — | — | — | — |
| Trisodium edetate | 0.05 | 0.05 | 0.05 | 0.05 | 0.05 |
| Perfume | 0.01 | 0.01 | 0.01 | 0.01 | 0.01 |
| Smoothness | A | A | A | A | A |
| Non-stickiness with dry-feeling | A | A | A | A | A |
| Supernatant white turbidity | A | A | A | A | A |
| Bottom caking state | A | A | A | A | A |
| Effect of dissolving and removing keratotic plugs | A | A | A | A | A |

TABLE 2

|  | Comparative Example 1 | Comparative Example 2 | Comparative Example 3 | Comparative Example 4 | Comparative Example 5 | Comparative Example 6 |
|---|---|---|---|---|---|---|
| Ion exchange water | Balance | Balance | Balance | Balance | Balance | Balance |
| Ethanol | 15 | 15 | 15 | 15 | 15 | 15 |
| Glycerin | 5 | 5 | 5 | 5 | 5 | 5 |
| 1,3-butylene glycol | 3 | 3 | 3 | 3 | 3 | 3 |
| PPG-13 decyltetradeceth-24 (HLB = 10) | 0.1 | 0.1 | — | — | 0.1 | 0.1 |
| Polyoxyethylene hydrogenated castor oil ((PEG = 60) (HLB = 14) *1 | — | — | — | 0.1 | — | — |

TABLE 2-continued

|  | Comparative Example 1 | Comparative Example 2 | Comparative Example 3 | Comparative Example 4 | Comparative Example 5 | Comparative Example 6 |
|---|---|---|---|---|---|---|
| Polyoxybutylene (15) polyoxyethylene (44) dimethyl dimer diol ether (HLB = 16) | — | — | — | — | — | — |
| polyoxyethylene (50) polyoxypropylene (40) block copolymer dimethyl ether (HLB = 17) | — | — | — | — | — | — |
| Polyglyceryl myristate (HLB = 15.7) | — | — | — | — | — | — |
| Bentonite*² | 0.2 | — | 0.2 | — | — | 0.2 |
| Aluminum magnesium silicate*³ | — | — | — | 1 | — | — |
| Cellulose powder*⁴ | 1 | 1 | 1 | 1 | — | 1 |
| Talc | — | — | — | — | 1 | — |
| Sodium chloride | 0.2 | 0.2 | 0.2 | 0.2 | 0.2 | 0.2 |
| Phenoxyethanol | 0.3 | 0.3 | 0.3 | 0.3 | 0.3 | 0.3 |
| Succinic acid | — | 0.35 | 0.35 | 0.35 | 0.35 | — |
| Sodium succinate | — | 0.15 | 0.15 | 0.15 | 0.15 | — |
| Citric acid | — | — | — | — | — | 0.15 |
| Sodium citrate | — | — | — | — | — | 0.35 |
| Trisodium edetate | 0.05 | 0.05 | 0.05 | 0.05 | 0.05 | 0.05 |
| Perfume | 0.01 | 0.01 | 0.01 | 0.01 | 0.01 | 0.01 |
| Smoothness | A | C | A | B | B | A |
| Non-stickiness with dry-feeling | A | B | A | B | B | A |
| Supernatant white turbidity | A | C | C | A | C | A |
| Bottom caking state | A | C | B | B | C | A |
| Effect of dissolving and removing keratotic plugs | C | A | A | A | A | B |

*¹ Trade name "NIKKOL HCO-60" (Nikko Chemicals Co., Ltd.)
*²Trade name "Bengel FW" (HOJUN YOKO CO., LTD.)
*³Trade name "Sumecton SA-2" (KUNIMINE INDUSTRIES CO., LTD.)
*⁴Trade name "Celluloflow C25" (CHISSO CORPORATION)

Referring to Tables 1 and 2, it is obvious that the feeling-in-use and powder-dispersion properties are excellent if succinic acid or sodium succinate is not contained (Comparative Example 1.) However, if succinic acid and sodium succinate are formulated (Comparative Example 2), not only the smoothness and non-stickiness with dry-feeling upon application are unsatisfactory but also white turbidity of supernatant and caking state at the bottom are poor, despite contained cellulose powder.

In contrast, as to redispersible powder-dispersed cosmetics containing succinic acid and sodium succinate, a bentonite, and a hydrophilic surfactant (Examples 1 to 5), the supernatant is clear on standing but powders easily disperse by shaking, feelings-in-use such as smoothness and non-stickiness with dry-feeling are excellent, and further an effect on dissolving and removing keratotic plugs is excellent.

In contrast, if a hydrophilic surfactant is not contained despite containing a bentonite (Comparative Example 3), the supernatant is turbid and dispersibility of the powders by shaking is poor. Further, if aluminum magnesium silicate instead of a bentonite, which is the same water-swellable powder as a bentonite, is used (Comparative Example 4), not only improvement of powder dispersibility is insufficient, but also feelings-in-use such as smoothness and non-stickiness with dry-feeling are unsatisfactory. Even if a talc that is a kind of powder and commonly used in cosmetics is formulated instead of a bentonite and/or cellulose powder (Comparative Example 5), the feeling-in-use upon application is unsatisfactory, and white turbidity of the supernatant and caking state at the bottom are poor. Further, if citric acid and sodium citrate, reportedly effective on dissolving and removing stratum corneum, are formulated instead of succinic acid and sodium succinate (Comparative Example 6), any sufficient effect on dissolving and removing keratotic plugs is not obtained.

Formulation Example

An example formulation of the redispersible powder-dispersed cosmetic of the present invention is disclosed below. Without saying, the present invention is not limited to the example formulation, but is identified by the claims. Further, all amounts in the formulation are represented in % by mass of the total amount of the product.

Example Formulation 1

Redispersible Powder-Dispersed Cosmetic

|  | (Component name) | Formulation Amount (%) |
|---|---|---|
| (1) | Purified water | Balance |
| (2) | Succinic acid | 0.3 |
| (3) | Sodium succinate | 0.1 |
| (4) | Sodium chloride | 0.1 |
| (5) | Trisodium edetate | 0.1 |
| (6) | Glycerin | 3 |
| (7) | Polyethylene glycol 400 | 1 |
| (8) | Butylene glycol | 3 |
| (9) | Purified water | 10 |
| (10) | Bentonite | 0.2 |
| (11) | Spherical cellulose powder | 1 |
| (12) | Ethanol | 12 |
| (13) | Polyoxyethylene hydrogenated castor oil | 0.1 |

-continued

| (Component name) | | Formulation Amount (%) |
|---|---|---|
| (14) | Phenoxyethanol | Appropriate amount |
| (15) | *Scutellaria baicalensis* extract | 0.1 |
| (16) | *Saxifraga sarmentosa* extract | 0.1 |
| (17) | Rose extract | 0.1 |

Preparation Method

Dissolve components (1) to (5) and then add components (6) to (8), and dissolve under stirring to obtain a water phase. Add dispersed-powders of component (9) to (11) dispersed by a disperser to the water phase under stirring. Add an alcohol phase obtained by dissolving components (12) to (14) to the water phase, and further add components (15) to (17) to obtain an intended redispersible powder-dispersed cosmetic.

What is claimed is:

1. A redispersible powder-dispersed cosmetic, comprising:
   (A) 0.05 to 5.0% by mass of succinic acid and/or a salt thereof,
   (B) 0.05 to 1.0% by mass of a bentonite, and
   (C) 0.05 to 1.0% by mass of a hydrophilic surfactant.
2. The redispersible powder-dispersed cosmetic, according to claim 1, further comprising:
   cellulose powder.

* * * * *

UNITED STATES PATENT AND TRADEMARK OFFICE
CERTIFICATE OF CORRECTION

PATENT NO. : 9,241,884 B2
APPLICATION NO. : 14/372896
DATED : January 26, 2016
INVENTOR(S) : Masayuki Shirao et al.

Page 1 of 1

It is certified that error appears in the above-identified patent and that said Letters Patent is hereby corrected as shown below:

In the Specification, column 1 line 4 the following correction is made:

Insert --CROSS REFERENCE TO RELATED APPLICATIONS--

--This application claims priority to International Ser. No. PCT/JP2012/083393 filed December 25, 2012, the entire contents of which are incorporated herein fully by reference, which in turn claims priority to JP 2012-275277 filed on December 18, 2012 and JP Ser. No. JP 2012-020547 filed February 2, 2012--

Signed and Sealed this
Nineteenth Day of April, 2016

Michelle K. Lee
*Director of the United States Patent and Trademark Office*